United States Patent [19]

Bickert et al.

[11] Patent Number: 5,540,087

[45] Date of Patent: Jul. 30, 1996

[54] APPARATUS FOR MEASURING THERMODYNAMIC CHARACTERISTICS OF A HYDROCARBON SAMPLE

[75] Inventors: Jacques Bickert, Roques; Karim Chaouche, Toulouse; Marcel Royer, Saint-Gaudens; Jose Sanchez, Viarmes, all of France

[73] Assignee: Elf Aquitaine Production, France

[21] Appl. No.: 311,585

[22] Filed: Sep. 23, 1994

[30] Foreign Application Priority Data

Sep. 30, 1993 [FR] France ................................. 93 11663

[51] Int. Cl.⁶ ........................................................ G01N 33/26
[52] U.S. Cl. .......................................... 73/53.05; 73/64.56
[58] Field of Search ........................................... 73/53.05

[56] References Cited

U.S. PATENT DOCUMENTS

| | | | |
|---|---|---|---|
| 2,380,081 | 7/1945 | Sloan | 73/19.01 |
| 2,380,082 | 7/1945 | Sloan | 73/19.01 |
| 4,395,902 | 8/1983 | Espenscheid et al. | 73/19 |
| 4,425,810 | 1/1984 | Simon et al. | 73/863.11 |
| 4,530,234 | 7/1985 | Cullick et al. | 73/53 |
| 4,539,837 | 9/1985 | Barnaby | 73/55 |
| 4,595,833 | 6/1986 | Sting | 250/353 |
| 4,783,989 | 11/1988 | Reed | 73/64.2 |
| 4,942,760 | 7/1990 | Almedia | 73/64.4 |
| 5,024,098 | 6/1991 | Petitjean et al. | 73/729 |
| 5,172,586 | 12/1992 | Reed | 73/64.45 |
| 5,303,775 | 4/1994 | Michaels et al. | 166/264 |
| 5,310,683 | 5/1994 | Godec et al. | 436/123 |
| 5,377,755 | 1/1995 | Michaels et al. | 166/264 |

FOREIGN PATENT DOCUMENTS

| | | | |
|---|---|---|---|
| 2593921 | 8/1987 | France | G01N 33/24 |
| 2687223 | 8/1993 | France | G01N 11/14 |
| 2188437 | 9/1987 | United Kingdom | G01N 7/14 |

Primary Examiner—Hezron E. Williams
Assistant Examiner—Jay L. Politzer
Attorney, Agent, or Firm—Bacon & Thomas

[57] ABSTRACT

Apparatus for measuring thermodynamic characteristics of a hydrocarbon sample, comprising at least one measurement cell (12; 14) intended to be selectively connected to a gas gauge (82); the gas gauge being capable of being selectively connected to a gas recovery assembly (98) and a liquid storage assembly (114), the measurement cell (12; 14) comprising a piston/cylinder assembly (16; 20; 18; 22), the piston being movable in the cylinder under the action of a jack (24; 26).

5 Claims, 2 Drawing Sheets

APPARATUS FOR MEASURING THERMODYNAMIC CHARACTERISTICS OF A HYDROCARBON SAMPLE

BACKGROUND OF THE INVENTION

1. Field of the Invention

The present invention relates to an apparatus for measuring thermodynamic characteristics of a hydrocarbon sample, more particularly intended for providing thermodynamic measurements relating to a deposit fluid sample coming from an oil well.

2. Description of Related Art

On discovering an oil field, samples of the deposit fluid are periodically taken in order to make it possible to measure the various physical and thermodynamic characteristics of the fluid. These measurements make it possible to characterize the deposit fluid and thus to optimize the production of the well by providing surface installations which are best suited to treating the fluids produced, by predicting the behavior of the fluid inside the deposit during production, as well as its behavior under the surface conditions as it is exploited.

The measurements taken from the sample make it possible to know the composition of the deposit fluid as well as its physical characteristics such as its viscosity cosity or its compressibility. The measurements taken also make it possible to predict the change in the composition of the gas in the deposit and to decide on the drainage and recovery mechanisms. In addition, by determining the change in the deposit fluid under the temperature and pressure conditions existing at the well bottom, the measurements make it possible to predict the production lifetime of the well. In fact, the pressure of the fluid in the reservoir rock decreases as a function of the production of the well and can thus fall to a level where the gases present in the reservoir rock start to condense.

The sampling of the deposit fluid, as well as the measurement of the characteristics of this fluid, should be carried out under very precise conditions, because the volume sampled for analysing it represents only a minute part of the fluid in the reservoir rock, and the physical properties measured can only be extrapolated validly to the deposit itself if this fraction is itself representative of the whole and if the measurements taken are exact.

There are two ways of taking samples of the deposit fluid; bottom sampling, which is generally carried out for oil deposits, and surface sampling which comprises sampling carried out at the test gas/oil separator. In the latter case, two samples are taken, one of gas and the other of oil, both under the pressure and temperature conditions of the separator, namely of the order of 40 bar and 30° C., that is to say markedly less than those existing at the well bottom. The deposit fluid is then reconstituted by recombining the liquid and gas fractions under the pressure and temperature conditions of the well bottom in order to measure the various characteristics of the sample.

These measurements are normally carried out in the laboratory, remote from the drilling site, using a measurement apparatus fitted with cells in which the temperatures and pressures of the well bottom are applied. In known measurement apparatuses, the measurement cells are connected to a mercury source allowing the fluid to be pressurized. The use of mercury has obvious drawbacks, in view of its toxicity and, furthermore, mercury-based systems do not make it possible to measure the deposit fluid volumes with sufficient precision.

SUMMARY OF THE INVENTION

The subject of the present invention is therefore an apparatus for measuring the characteristics of a hydrocarbon sample which has improved precision and which does not require the use of toxic elements such as mercury.

For this purpose, the invention proposes an apparatus for measuring thermodynamic characteristics of a hydrocarbon sample, comprising at least one measurement cell intended to be selectively connected to a gas gauge; the gas gauge being capable of being selectively connected to a gas recovery assembly and a liquid storage assembly, the measurement cell comprising a piston/cylinder assembly, the piston being movable in the cylinder under the action of a jack.

In addition, in apparatuses hitherto known, the dew point is defined visually in a cell having an inspection port using endoscopy. This technique, the assessment of which is subjective, unavoidably leads to a non-negligible margin of error.

A further subject of the present invention is a detection apparatus which makes it possible to determine the dew point of a sampled gas with increased precision.

For this purpose, the invention proposes a gas/liquid detection apparatus arranged in a measurement cell of the measurement apparatus, the said detection apparatus including a tubular element made of transparent material, comprising a conical end intended to project inside the cell, the tubular element being provided with an input and with an output for a light signal.

Other characteristics and advantages of the present invention will emerge more clearly on reading the description hereinbelow, made with reference to the attached drawings.

BRIEF DESCRIPTION OF THE PREFERRED EMBODIMENT

Figure 1:
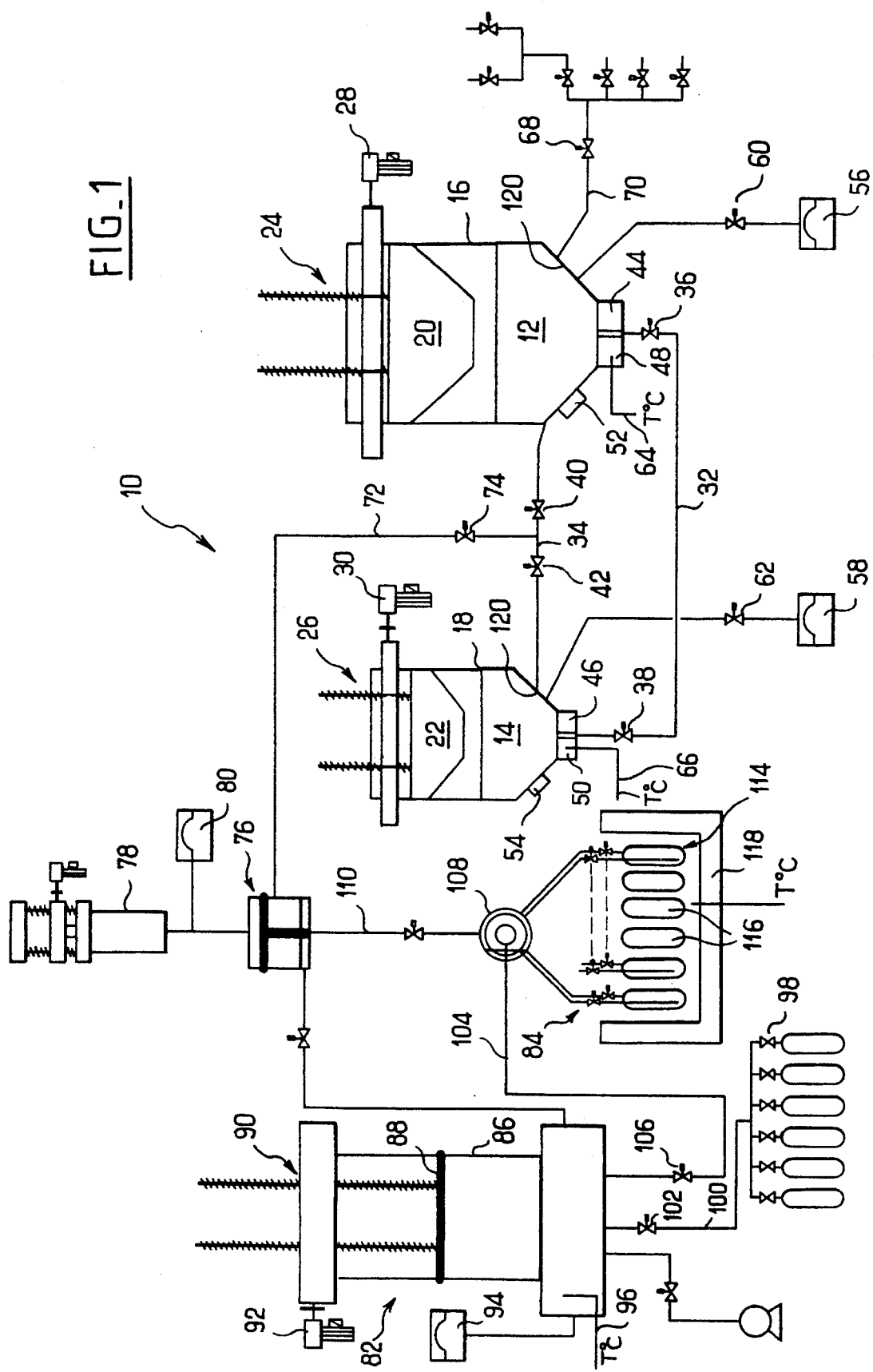
FIG. 1 is a diagram of a measurement apparatus according to the invention.

As represented in FIG. 1, an apparatus for measuring the thermodynamic parameters of a hydrocarbon sample, represented overall at 10, includes a first high-pressure cell 12 and a second high-pressure cell 14. Each cell is mounted vertically and comprises a generally cylindrical enclosure 16, 18 made of stainless steel, fitted with a piston 20, 22 mounted to slide in leaktight manner. The pistons 20, 22 can be moved inside the enclosures 16, 18 under the effect of ball-screw jack assemblies 24, 26 respectively, each assembly 24, 26 being driven by an associated electric motor 28, 30. The cells 12 and 14 are dimensioned for a working pressure of 1500 bar and a temperature of 230° C. and are connected together by pipes 32 and 34 each fitted with two motorized valves 36, 38 and 40, 42.

The lower part of each cell 12, 14 is fitted with a fibre-optic gas/liquid detection apparatus 46, respectively, which will be described in more detail hereinbelow and with an ultrasonic agitation system 48, 50 respectively which comprises a piezoelectric cell connected to an ultrasonic amplifier (not shown).

In the example illustrated, the cell 12 has a volume of 700 cm³, while the cell 14 has a volume of 110 cm³.

The cells 12 and 14 are fitted with internal pressure sensors 52, 54 with flush-fit diaphragm, without dead volume, responding to a range of from 0 to 2000 bar and similar pressure sensors 56, 58, responding to a range of 0 to 2000 bar, respectively connected to the bells 12 and 14 via pipes which include manual valves 60 and 62 with reduced dead volume. The cells 12, 14 each furthermore include a temperature probe 64, 66.

A motorized valve 68, arranged in a pipe 70 which emerges in the cell 12 is intended to control the inlet of fluid into the cell. The pipe 34 is connected, at a point lying between the valves 40 and 42, via a pipe 72 fitted with a motorized valve 74, to a differential valve 76, the opening of which is controlled by a motor assembly 78 similar to those used in the cells 12 and 14, including a pressure sensor 80. The differential valve 76 is intended selectively to connect the pipe 72 to a gas gauge, generally represented at 82 and a cold-treatment assembly, generally represented at 84.

The gas gauge 82 comprises a cell 86 of generally cylindrical shape, fitted with a piston 88 mounted to slide in leaktight manner and movable under the effect of a ball-screw jack assembly 90 driven by an electric motor 92. The cell 86 comprises a pressure sensor 94 and a temperature probe 96. In the example illustrated, the cell 86, which has a volume of 20 liters, is dimensioned for a maximum static pressure of 15 bar and a temperature of 230° C. for a working pressure of 4 bar.

The cell 86 can be selectively connected to a gas recovery assembly which, in the example illustrated, comprises bottles 98, via a pipe 100 fitted with a motorized valve 102. In addition, the cell 86 can be selectively connected to the cold-treatment assembly 84 via a pipe 104 fitted with a motorized valve 106. This assembly 84 comprises a valve 108 of the chromatograph type, capable of selectively communicating with the pipe 104, the differential valve 76 via a pipe 110, and a common inlet 112 of a liquid storage assembly 114 which, in the example illustrated, comprises six bottles 116 arranged in a thermostatically controlled glycol bath 118 which cools and heats the bottles 116 between, for example, −30° C. and 50° C. The liquid storage assembly 114 is arranged inside a climatic enclosure, not shown, with another climatic enclosure, not shown, containing the cells 12 and 14, the differential valve 76 and the gas gauge 82.

Figure 2A:
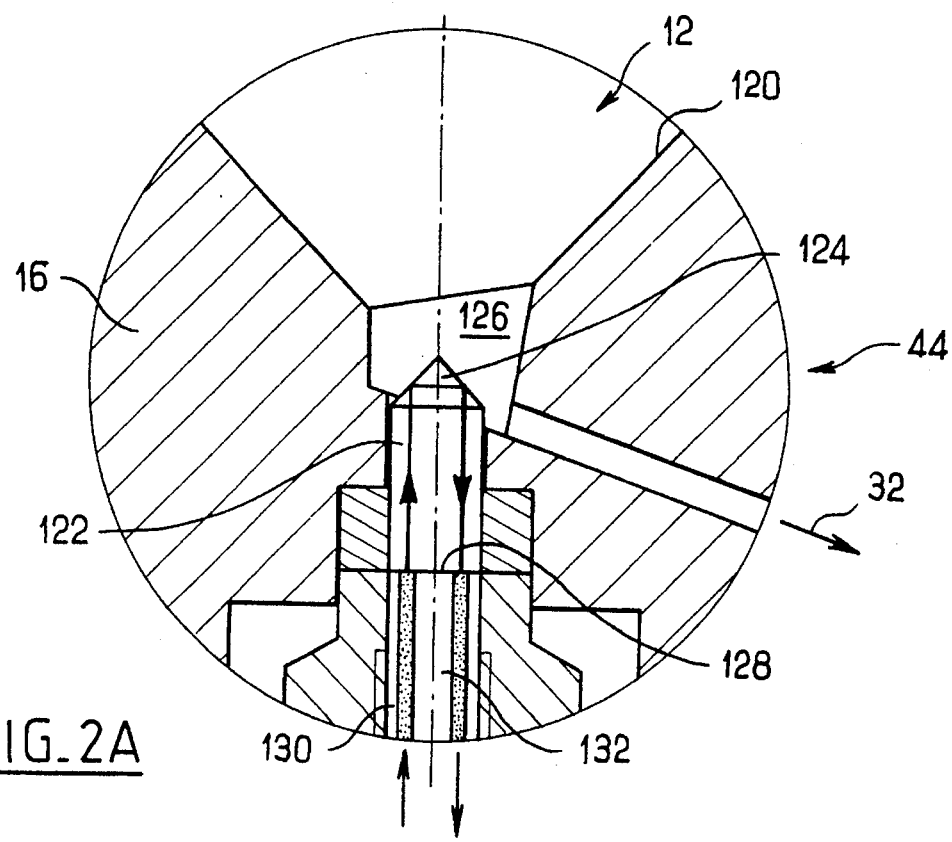
FIGS. 2A and 2B are each a view in longitudinal section of a fibre-optic gas/liquid detection apparatus.
Figure 2B:
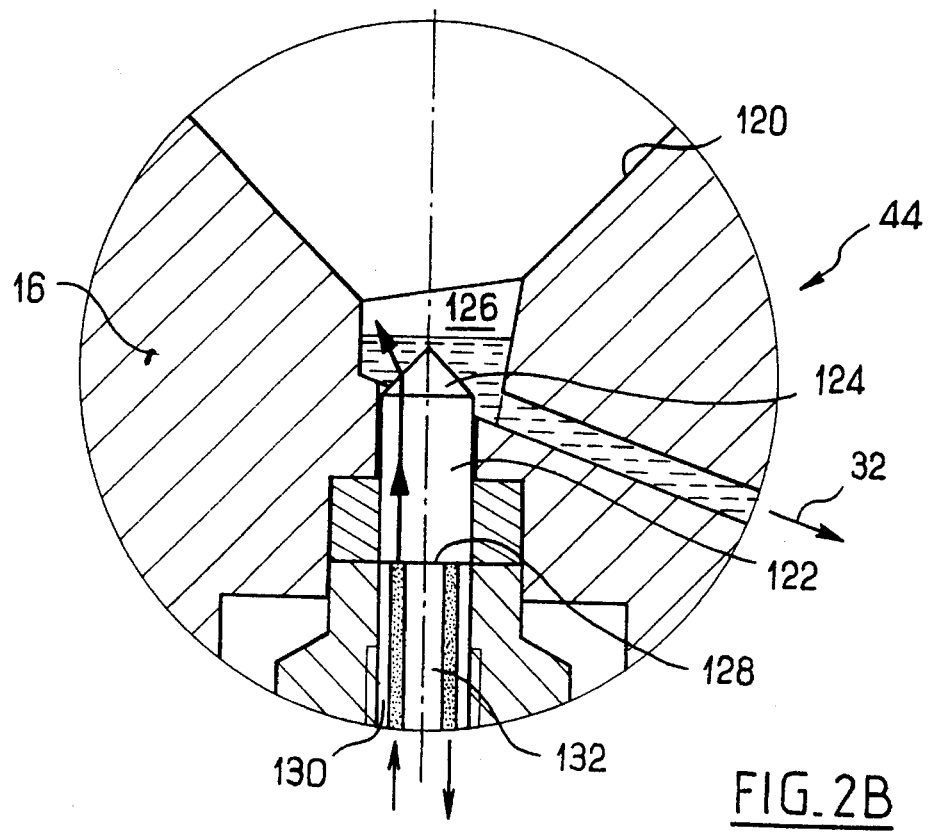

As shown in FIGS. 2A and 2B, a fibre-optic gas/liquid detection apparatus 44 is mounted on the lower end of a conical part 120 of each of the cells 12 and 14. Each apparatus 44 comprises a tubular element 122 having a conical end 124 which projects into a detection chamber 126 formed in the apex of the conical part of the cells 12 and 14. The element 122 is made of transparent material which, in a preferred embodiment, is sapphire. The end 128 of the tubular element 122 which lies opposite the conical end 124 defines a plane normal to the longitudinal axis of this element. This end is optically connected to two fibre-optic cables 130, 132, one 130 forming a light input to the element 122 and the other 132 forming a light output.

FIG. 2A shows the gas/liquid detection apparatus 44 in the absence of liquid in the detection chamber 126, the cell 12 containing only gas. A light signal, arriving via the input fibre-optic cable 130, is reflected by the inclined surface of the conical end 124 and reemerges via the output fibre-optic cable 132.

When the conditions in the cell 12 cause condensation of the gas present in the cell, droplets of liquid form and accumulate in the detection chamber 126. As soon as liquid droplets are deposited on the surface of the conical end 124, the beam of the light signal which arrives via the input fibre-optic cable 130 is refracted out of the element 122, which has the result that there is no longer a return signal travelling via the output fibre-optic cable 132. The detection apparatus thus makes it possible to determine, with increased precision, the dew point of the sampled gas. The volume of liquid present in the detection chamber 126, before the level of the liquid reaches the conical surface 124, is equal to the dead volume of the cell 12. It should be remembered that the, shape of the piston 12 is complementary to that of the inside of the cylindrical enclosure 16. This dead volume, determined before the apparatus is first used, is negligible compared to the volume of the cylindrical enclosure 12.

Preferably, the pistons 20 and 22 each comprise a body and a head (not shown), a seal being clamped between the body and the head. This seal comprises a plurality of washers made of different plastics.

The measurement apparatus according to the invention makes it possible to reach pressure and temperature levels which are markedly greater than those used in apparatuses hitherto known.

The Invention claimed is:

1. Apparatus for measuring thermodynamic characteristics of a hydrocarbon sample, comprising at least one measurement cell for measuring pressure, volume and temperature characteristics of the hydrocarbon sample, said measurement cell being selectively connected to a gas gauge for measuring pressure, volume and temperature characteristics of a gaseous sample received from said measurement cell; said gas gauge being selectively connected to a gas recovery assembly and a liquid storage assembly for recovering and storing gas and liquid from said gas gauge for subsequent analysis, said measurement cell comprising a piston/cylinder assembly, the piston being movable in the cylinder under the action of a jack and a gas/liquid detection apparatus arranged in said measurement cell, said detection apparatus including a tubular element made of transparent light transmitting material, comprising a conical end projecting inside the cell, the tubular element being provided with an input and an output for a light signal.

2. Apparatus according to claim 1, wherein the shape of the piston is complementary to that of the interior of the cylinder in order to reduce the dead volume of the piston/cylinder assembly to a minimum.

3. Apparatus according to claim 1 wherein the jack is a ball-screw jack.

4. Apparatus according to claim 1, wherein it comprises two cells, each being capable of being connected to the gas gauge, the two cells being arranged to be selectively connected together.

5. Apparatus according to claim 1, wherein the tubular element is made of sapphire.

* * * * *